United States Patent [19]

Skadeland

[11] 4,301,147

[45] Nov. 17, 1981

[54] DISPERSAL OF PATHOGENIC MATERIAL FOR PEST CONTROL

[76] Inventor: David A. Skadeland, Rte. 5, Planatation Rd., Fayetteville, Ga. 30214

[21] Appl. No.: 918,723

[22] Filed: Jun. 26, 1978

[51] Int. Cl.$^3$ ..................... A01N 25/00; A01N 63/00
[52] U.S. Cl. ......................................... 424/93; 424/84
[58] Field of Search ................................... 424/84, 93

[56] References Cited

U.S. PATENT DOCUMENTS

| | | | |
|---|---|---|---|
| 3,087,865 | 4/1963 | Drake et al. | 424/93 |
| 3,337,395 | 8/1967 | Page | 424/93 |
| 3,420,933 | 1/1969 | Cords | 424/84 |

Primary Examiner—Allen J. Robinson
Attorney, Agent, or Firm—James B. Middleton

[57] ABSTRACT

A method for controlling Japanese beetles through the spreading of spore dust to innoculate the ground with spores for causing milky disease in larvae of Japanese beetles by luring Japanese beetles into a container, directing the beetles into a second container where the beetles are immersed into the spore dust, and providing escape means to allow the beetles to escape and spread the spore dust through their natural activity, and the apparatus described for so treating the beetles.

2 Claims, 2 Drawing Figures

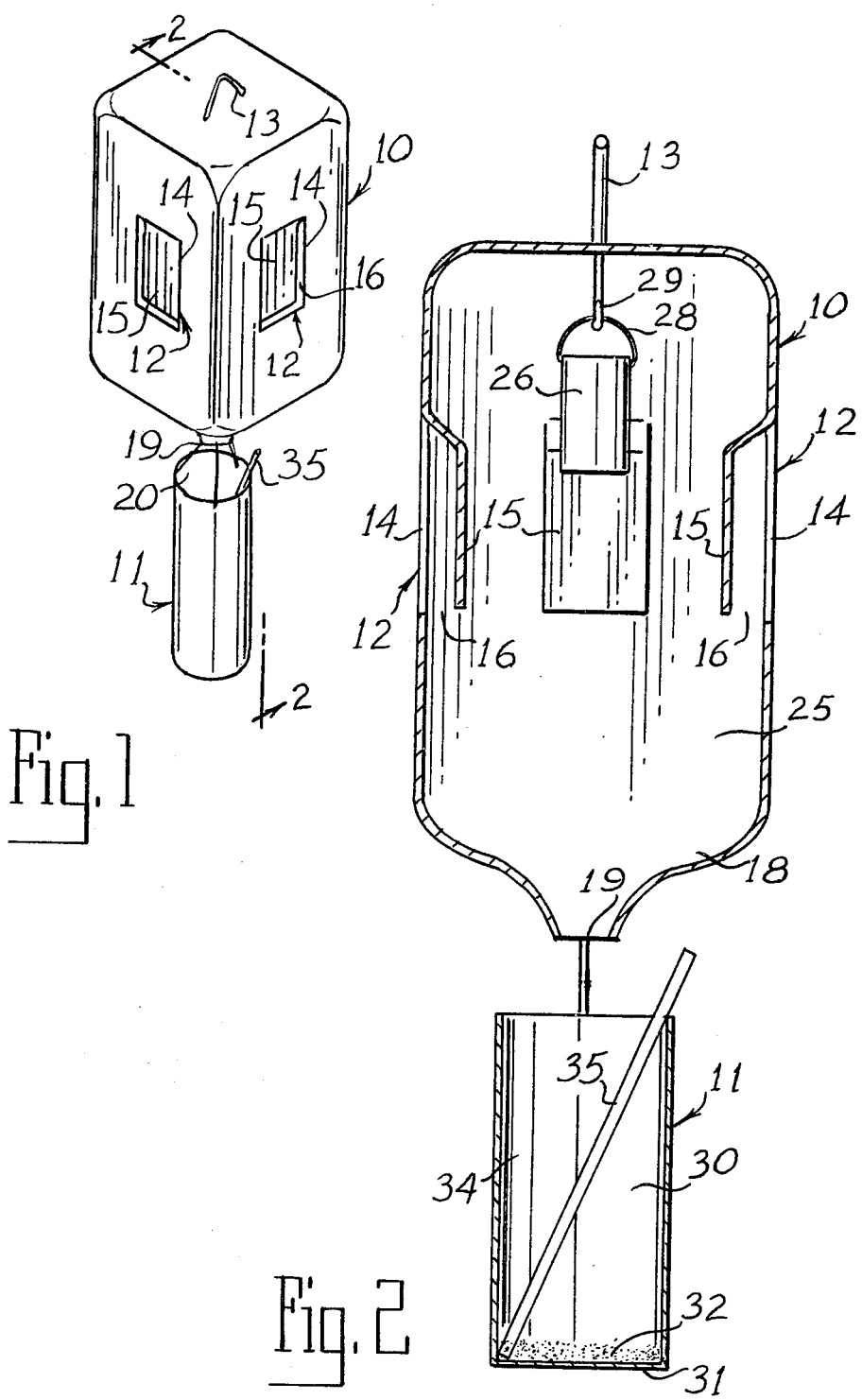

DISPERSAL OF PATHOGENIC MATERIAL FOR PEST CONTROL

This invention relates generally to the control of pests, and is more particularly concerned with a method and apparatus for distributing disease causing spores for the control of insect larvae.

Since its introduction into the United States, the Japanese beetle has been a destructive pest. The adult beetles are destructive pests in that they eat many forms of vegetation including fruit trees, ornamental shrubs and the like. The Japanese beetle is also destructive in the larval stage in that an egg is laid underground by an adlt beetle, and the larva feeds on the roots of grass and other vegetation in the vicinity.

After many years of efforts to find some means for the control of Japanese beetles, including the investigation of predators, parasites and diseases, a disease of the larva was discovered and named "Milky Disease". This milky disease, on investigation, was found to be caused by several different varieties of spore forming bacteria which grow and sporulate in the blood of grubs. A relatively high concentration of spores in the blood of the grubs causes the blood to have a milky appearance, and this infestation causes the death of the grub. The spores which cause milky disease have been found to survive a wide range of conditions so that the spores are desirable for use in controlling the Japanese beetle. Also, these spores have now been produced in large quantity and mixed with talc for distribution and colonization in ground areas. The usual method for use of the spore-talc mixture (commonly known as spore dust) is to place small quantities of the spore dust in discrete piles, distributed over an area to be treated. The natural action of the weather as well as the area's animal life gradually distributes the spore dust so that these spores colonize a large area of ground. When eggs are laid in the ground, the eggs change into the larval stage, and the larva, or grub, feeds on the spores. The spores increase sufficiently to cause death of the grub.

While the above outlined procedure has been found to be effective in controlling the grubs in a given area, the prior art methods for innoculating the ground sufficiently to be effective has been very expensive, and time consuming. Additionally, if one property owner incurs the expense to treat his land but adjacent property owners do not, the expense is not justified because there will be adult beetles in the area that will damage trees and the like. The cost of treatment of the land by prior are methods has been prohibitive to some property owners, so it has been very difficult to have a community effort in treating the ground. There are some less expensive methods for controlling the Japanese beetle, but these involve the use of highly toxic substances such as chlordane. While chlordane will kill Japanese beetles, the substance is extremely toxic to virtually all animal life, including humans, so that its wide-spread use is undesirable. Furthermore, if colonization of the milky disease spores is started, use of chlordane in the same area tends to kill the bacteria and limit the further colonization. Thus, the use of milky disease to control Japanese beetles is most desirable, but the prior art has not provided an effective and inexpensive method or apparatus for spreading the disease.

The present invention overcomes the above mentioned and other difficulties with the prior art by providing a direct contact method for dispersing disease causing spores, and by providing very simple apparatus for carrying out the method. Briefly, the method of the present invention includes the steps of arresting adult pests, treating the pests with spore-containing dust, and allowing the treated pest to go free. The pest thereby contaminates its habitat with the disease-causing spores. The apparatus includes a container into which the pests are lured, means for directing the pests into a spore-containing dust, and escape means for allowing the pests to escape.

These and other features and advantages of the present invention will become apparent from consideration of the following specification when taken in conjunction with the accompanying drawing in which:

FIG. 1 is a perspective view of one form of apparatus made in accordance with the present invention for arresting and treating pests; and, FIG. 2 is an enlarged longitudinal cross-sectional view of the device shown in FIG. 1.

Referring now more particularly to the drawing, and to that embodiment of the invention here chosen by way of illustration, the treatment device shown in FIG. 1 comprises an upper container 10 and a lower container 11. The upper container 10 includes somewhat guarded entrances 12 which allow relatively easy ingress of flying pests, but provide for rather difficult egress of the pests. While numerous such arrangements may be used, the particular arrangement here shown includes a large opening 14 in a relatively flat wall of the container 10. Behind the opening 14, there is a tab or baffle 15, connected along its upper edge to the upper side of the opening 14. The tab 15 is generally the same size as the opening 14, and is spaced slightly rearwardly of the opening 14 so that a small slit-like space 16 is provided on three sides of the tab 15 for relatively easy ingress of pests. Those skilled in the art will realize that, once inside the container 10, the pests will not readily find their way out through the slit-like space 16.

The lower portion of the container 10 is somewhat funnel shaped, the bottom 18 of the container 10 terminating in a relatively small opening 19; and, it will be seen that the opening 19 is substantially axially aligned with the container 11 so pests that find their way into the upper container 10 will naturally pass through the lower opening 19 and into the opening 20 of the container 11.

The container 11 is cylindrically shaped, and is preferably of a substantial height relative to its diameter. The container 11 is closed on all sides except for the top 20 which is completely open. As a result, the interior of the container 11 will be shaded except at the extreme upper end. When the sun is almost directly above the container 11, the container 11 will be shaded by the large container 10.

Looking now at FIG. 2 of the drawing, it will be seen that the interior 25 of the container 10 includes a bait cup 26 which may be fixed within the container 10 in any desired manner. The bait cup 26 is here shown as having a bail 28 for hanging the cup 26 from a hook or the like 29 fixed to the upper surface of the upper container 10. Those skilled in the art will readily recognize that scented bait is well known in the art and is quite effective in attracting Japanese beetles and similar pests. Therefore, with an appropriate bait in the bait cup 26, pests will pass through the opening 14, and through the slit 16 to be within the interior 25 of the upper container 10. Since the pests cannot then find their way back through the slit 16, they will pass through the funnel shaped bottom 18 of the container 10, then through the narrow opening 19 to pass directly to the interior 30 of the lower container 11. Passing through the opening 19, the pests will be falling rather than flying, so they will reach the bottom 31 of the container 11. The container 11 has a quantity of dust indicated at 32, the quantity being such that every pest that falls into the lower container 11 must be well dusted with the dust 32.

At this point it should be understood that the present invention is concerned largely with the control of the Japanese beetle, *Popillia japonica,* and that the control is through spread of spores that cause milky disease. Milky disease is caused by spore producing bacteria such as *Bacillus popillae* and *Bacillus lentimorbus,* and other similar bacteria and varieties of these bacteria. However, both the method and the apparatus of the present invention are equally applicable to the spread of other pathogenic material by various pests. Nevertheless, for purposes of illustration, the Japanese beetle will be referred to as the pest, and spore dust containing spores of bacteria that cause milky disease in beetle grubs will be referred to as the pathogenic material.

Since Japanese beetles will not be able to climb the vertical walls 34 of the lower container 11, an escape means 35 is provided in the lower container 11. The lower container 11 is made preferably of metal or other opaque material, the opacity being predominately to ultra-violet radiation. While the beetles could climb the wall if the container 11 were made of highly fibrous material, screen wire, fabric or the like, the object is to have a lower container 11 that will protect the spore dust 32 for a maximum useful life. Since ultra-violet radiation is the principal ambient condition that harms the spores, the container 11 is made to exclude this radiation as discussed above. Obviously, the container 11 must be impervious so that the spore dust 32 will not sift through the walls of the container. Thus, an escape means 35 can be of any substance that will allow the beetles to walk out of the container 11. Most commonly, the escape means 35 will be simply a wooden rod or the like.

With the foregoing description in mind, it will be seen that the upper container 10 would be suspended from any convenient means by the hanger 13, a quantity of spore dust 32 would be placed in the lower container 11, and a quantity of Japanese beetle bait would be placed in the bait cup 26. Beetles will then be attracted by the bait in the bait cup 26, and will enter the upper container 10. Being unable to find their way out through the slits 16, the beetles will pass down the funnel shaped bottom 18 and through the narrow exit opening 19 of the container 10 to fall into the lower container 11 and into the spores dust 32. After this, the beetles will find their way up the escape means 35 which extends sufficiently beyond the lower container 11 to allow the beetles room to spread their wings and fly away.

Once a beetle has been dusted with the spore dust 32, wherever the beetle lights, or stops briefly, will be innoculated with some of the spore dust carried by the beetles. Most importantly, when a female beetle is dusted with the spore dust 32, the area in which eggs are laid will be infected with the spore dust; and, it is likely that the eggs themselves will be infected to some extent with the spore dust.

It appears that the eggs themselves are not affected directly by the spore dust; however, when the eggs are transformed into the larval stage and the larva, or grub, begins to eat the surrounding vegetation in the soil, the grub will ingest some of the spores. Though the precise mechanism appears not to be well understood, it is known that when a grub ingests spores of the bacterium that causes milky disease, the grub eventually tends to have spores in its blood, and the spores multiply and become sufficiently numerous that the grub will die.

It is known in the art that a grub in an area colonized with spores will not necessarily have milky disease and be killed by it; however, it is rather well established that there is simply a probability relationship as to whether or not the grub will get milky disease. As a result, the greater the colonization, the more likely is a grub to get milky disease.

This probability relationship renders the method of the present invention extremely important as a means to assure a great extent of colonization by the bacteria and the spores. Since the method of the present invention depends on dispersal of the spore dust by the beetles themselves, the greater the population of Japanese beetles, which is to say the greater the problem with Japanese beetles, the greater will be the spreading of the spore dust.

From the foregoing discussion, it should be understood that when the treating means as shown in the drawing are placed for treating the Japanese beetles, the treating means should be placed as far from trees and other vegetation to be protected as is reasonably possible. Since the treatment in accordance with the present invention does not kill the adult beetle, vegetation is still subject to damage unless the vegetation itself is treated with soap solution or other chemical means to prevent attack by adult Japanese beetles.

Using the method of the present invention, it will be understood that the method would be most effective when used by a community rather than by one property owner. Everyone in a community will benefit from the use of the method by any property owner, but the more beetles that can be treated in a given geographical area, the wider will be the dispersal of the spore dust, and the greater will be the effectiveness of the method. Due to the nature of the dispersal of the spore dust, it will be understood that a very small quantity of spore dust is required for the treatment. In general, one or two teaspoons of spore dust will be placed in the lower container 11 of the treating means, and the spore dust 32 will generally remain active so that it must simply be replaced as it is dispersed by the beetles. As a result, a small quantity of spore dust will last throughout an entire season.

While the method of the present invention has been described primarily in conjunction with the treating means shown in the drawing, it should be equally well understood that the method can be used with virtually any conventional Japanese beetle trap. For the method to be effective, however, one must alter the trap as necessary to assure that the beetles are not killed while in the trap; rather, the beetles should remain alive, and should be well dusted with spore dust and then released. This would yield precisely the same result but would require more attention to the traps.

It will of course be understood by those skilled in the art that the particular embodiment of the invention here chosen is by way of illustration only, and is meant to be in no way restrictive; therefore, numerous changes and modifications may be made, and the full use of equivalents resorted to without departing from the spirit or scope of the invention as defined by the appended claims.

I claim:

1. In the method of controlling Japanese beetles wherein the ground is innoculated with spore dust, said spore dust comprising an inert dust and spores for causing milky disease in the larvae of Japanese beetles, larvae of Japanese beetles ingest said spores and die from milky disease, the improvement including the steps of luring adult Japanese beetles into a container with bait, directing said adult Japanese beetles into a sufficient quantity of said spore dust that said adult Japanese beetles are substantially immersed in said spore dust, and allowing said adult Japanese beetles to escape from said quantity of spore dust and act as a carrier to distribute the spore dust that clings to said adult Japanese beetles to effect said innoculation of the ground.

2. The method as claimed in claim 1, and further characterized by the step of protecting said quantity of said spore dust from direct sunlight.

* * * * *